United States Patent
Wiedenbrueg et al.

(10) Patent No.: US 12,022,259 B2
(45) Date of Patent: *Jun. 25, 2024

(54) SYSTEM, METHOD AND COMPUTER PROGRAM FOR INTERACTIVELY ASSISTING A USER IN EVALUATING A HEARING LOSS

(71) Applicants: Sivantos Pte. Ltd., Singapore (SG); Widex A/S, Lynge (DK)

(72) Inventors: Cornelia Wiedenbrueg, Spardorf (DE); Ulrich Giese, Fuerth (DE); Stefan Aschoff, Eckental (DE); Svend Vitting Andersen, Espergaerde (DK)

(73) Assignees: Sivantos Pte. Ltd., Singapore (SG); Widex A/S, Lynge (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/160,481

(22) Filed: Jan. 27, 2023

(65) Prior Publication Data
US 2023/0171552 A1 Jun. 1, 2023

Related U.S. Application Data

(63) Continuation of application No. 17/552,356, filed on Dec. 16, 2021, now Pat. No. 11,683,649.

(30) Foreign Application Priority Data

Dec. 16, 2020 (EP) .................................. 20214521

(51) Int. Cl.
H04R 25/00 (2006.01)

(52) U.S. Cl.
CPC ........... *H04R 25/305* (2013.01); *H04R 25/50* (2013.01); *H04R 2225/39* (2013.01); *H04R 2499/11* (2013.01); *H04R 2499/15* (2013.01)

(58) Field of Classification Search
CPC ...... H04R 25/00; H04R 25/30; H04R 25/305; H04R 25/43; H04R 25/50; H04R 25/55
See application file for complete search history.

(56) References Cited

U.S. PATENT DOCUMENTS

| 8,761,421 B2 | 6/2014 | Apfel |
| 9,473,862 B2 | 10/2016 | Stromsted |

(Continued)

FOREIGN PATENT DOCUMENTS

| EP | 3621316 A1 | 3/2020 |
| JP | 2016525315 A | 8/2016 |

(Continued)

*Primary Examiner* — Suhan Ni
(74) *Attorney, Agent, or Firm* — Laurence A. Greenberg; Werner H. Stemer; Ralph E. Locher

(57) ABSTRACT

A system, method and computer program are configured to interactively assist a user in evaluating and/or configuring a hearing aid. The system is equipped with a display element, with an input unit and with a processing unit. The environmental situations are shown on the display element. Based on a user input, a selected section of the environmental situation is determined and highlighted. A specific hearing situation is presented on the basis of the selection made by the user. An evaluation scale is displayed, allowing the user to enter a hearing value for a self-assessment of his hearing ability for the specific hearing situation, and the hearing value entered by the user is recorded. The above steps are repeated and hearing values are recorded for different specific hearing situations. Based on the hearing values entered by the user, setting values for the hearing aid are determined.

18 Claims, 3 Drawing Sheets

(56) References Cited

U.S. PATENT DOCUMENTS

| | | |
|---|---|---|
| 2010/0272297 A1 | 10/2010 | Boretzki |
| 2015/0023535 A1 | 1/2015 | Shennib |
| 2017/0099550 A1 | 4/2017 | Blessing et al. |
| 2020/0084555 A1 | 3/2020 | Dierks et al. |

FOREIGN PATENT DOCUMENTS

| | | |
|---|---|---|
| JP | 6172462 B2 | 8/2017 |
| JP | 2020061731 A | 4/2020 |
| WO | 2008154706 A1 | 12/2008 |
| WO | 2019233602 A1 | 12/2019 |

6, 8, 10, 12A

20

22

SYSTEM, METHOD AND COMPUTER PROGRAM FOR INTERACTIVELY ASSISTING A USER IN EVALUATING A HEARING LOSS

CROSS-REFERENCE TO RELATED APPLICATION

This application is a continuation of patent application Ser. No. 17/552,356, Filed Dec. 16, 2021; this application also claims the priority, under 35 U.S.C. § 119, of European Patent Application EP 20 214 521.5, filed Dec. 16, 2020; the prior applications are herewith incorporated by reference in their entireties.

FIELD AND BACKGROUND OF THE INVENTION

The invention relates to a system, a method and a computer program for the interactive support of a user, in particular a hearing-impaired user, in evaluating a hearing loss and especially for a configuration, in particular for an initial configuration of a hearing aid.

Hearing aids are generally understood to be devices which compensate for the hearing deficits of a hearing-impaired person. In particular, such a hearing aid has a user-specific frequency-dependent amplification function, which depends on the individual hearing impairment. Modern hearing aids also have many other functions.

To achieve a satisfactory hearing result, each hearing aid must be individually adapted to the user. In addition to different types of hearing aids which differ in terms of their design, the hearing aid must be parameterised with regard to its hearing aid functions, especially with regard to the individual frequency-dependent amplification function. Therefore, setting values for adjustment parameters must be determined individually and transferred to the hearing aid.

Nowadays, hearing aids are usually adjusted by an audiologist. In order to identify the individual hearing impairment, it is often done in such a way that the user, i.e. the hearing-impaired person, is offered different hearing samples. The user evaluates how he or she perceives these sound samples. These sound samples are, for example, speech samples, music samples or other sounds or noises.

Overall, the determination of the individual hearing impairment and the determination of the necessary settings for adjusting the hearing aid is complex and time consuming. This is often an inhibition threshold for first-time users, who do not yet have a hearing aid. This often leads to the fact that these first-time users, despite being hearing impaired, do not use a hearing aid, which can lead to negative impacts to their social relations.

SUMMARY OF THE INVENTION

Based on the above, the invention is intended to simplify the configuration, in particular the initial configuration of a hearing aid especially for first-time users.

According to the invention, the task is solved by a system, a method and a computer program to support a user, in particular a hearing-impaired user, in the evaluation of a hearing loss of the hearing-impaired user and especially in the (initial) configuration of a hearing aid. The advantages and preferred configurations listed below in connection with the system are also to be applied analogously to the method and the computer program. The system contains generally one or more devices which are specially designed to carry out the procedure. The system contains:

a) a display element for showing an image showing an environmental situation. This image is in particular a representation of the real environment. The image of a real environment is understood to be, for example, a photograph but also an animated representation in which the environment, i.e. people, buildings, streets, vehicles, etc. are reproduced in a natural manner.

b) an input unit for detecting a user input and especially for selecting a section of the environmental situation presented on the basis of a user input. This input unit is designed, for example, as a touch screen, as a separate input device such as a keyboard or a mouse, or is designed to receive voice commands or to gesture commands.

c) a processing unit for controlling the display unit and for processing the user input. The processing unit is usually a computer unit, i.e. a processor with the usual associated components, such as memory, graphic card for controlling the display element, interfaces for the user inputs, etc. The processing unit can also be distributed over several different hardware devices.

The processing unit is configured to perform the following steps, which also characterise the process. The computer program has commands that, when the program is executed by the system, cause this system to perform the following steps depending on the user input:

a) the environmental situations are displayed on the display element, b) based on a user input a selected section (16) of the environmental situation is determined and highlighted, c) a specific hearing situation is displayed on the basis of the selection made by the user, d) an evaluation scale is displayed, on the basis of which the user can enter a hearing value for a self-assessment of his hearing ability for the specific hearing situation and a hearing value entered by the user is recorded, e) steps a) to d) are repeated and hearing values are recorded for different specific hearing situations in each case and optionally, f) setting values for the hearing aid are determined on the basis of the hearing values entered by the user.

This procedure has the advantage that an interactive interface is provided by the pictorial natural representation of environmental situations and the graphically animated user interaction, which can be operated intuitively and playfully by the user. At the same time, the first relevant information about a hearing impairment of the user is recorded, especially in dependence of different environmental situations and thus hearing situations.

The evaluation scale, which is displayed in the image of the selected specific and pictorially represented hearing situation, contains, for example, pictorial symbols in the form of smileys, a grading scale or a displayed control panel. Pictorial symbols are preferably used.

By repeatedly selecting specific sections from the image that relate to specific hearing situations, the user performs a self-assessment for different hearing situations. On this basis, the system determines the setting values, especially for an individual frequency-dependent amplification function, which are then used for the further configuration of the hearing aid.

The proposed system as well as the proposed method is used:

a) (only) to assist the user for an evaluation of the users hearing loss;

b) optionally in addition with the configuration of an hearing aid based on the evaluation of the hearing loss in Step a), wherein:
c) the configuration might be a (initial) configuration input for a first basic configuration of the hearing aid, for example a hearing aid which is purchased; and
d) alternatively or in addition the configuration might be a fine tuning of an already configured hearing aid which is already used by the user (wearer), for example to adapt the hearing aid to new listening situations, especially to adapt the hearing aid to a new listening behaviour of the wearer.

The system and the method are for example also used in the trial phase during the buying process at an audiologist. Additionally or alternatively the system and the method are used for hearing aid evaluations hearing aid studies.

Preferably no sound sample is offered with this system and procedure. This means that only the self-assessment made by the user with regard to the different pictorially represented specific hearing situations is used to determine the settings. In this respect, there is no "measuring" of the user's hearing damage by offering and evaluating sound samples, such as speech, music, sounds, noises, etc.

Preferably, the system contains a local device, especially a portable device such as a tablet or smartphone. Alternatively, to the device can be a local PC. The tablet, smartphone or PC may have the computer program installed, which controls the process. In general, user input is made via this local device. The local device contains the input element, the display element as well as the input unit and at least part of the processing unit. According to a first embodiment an application (computer program) is installed on the local device, performing all steps for assisting the user. In this case the processing unit of the local device is the only processing unit of the system.

Alternatively, to an installation on a local device a split system is provided with the local device and a remote device. For example, a web-based solution is used, which the user can control via an Internet browser. In this case the application is installed or hosted on the remote device. In general, the processing unit is physically divided into a local part and a remote part in the case of such a split system.

Preferably the user is assisted only by the electronical system without any interaction with a human, e.g. a health care professional like an audiologist.

According to a preferred alternative the user is assisted by a human, e.g. a health care professional like an audiologist. Preferably the user and the health care professional are remote of each other. The remote device contains a further display element. Especially for this situation on the display element and on the further display element the same is displayed. This ensures that the audiologist is able to follow the user interactions and that the user and the audiologist see the same picture.

Preferably, the section selected by the user is highlighted in the image. According to one design variant, for example, a so-called "spot technique" is used for this purpose, in which the selected area is highlighted in the manner of a cone of light.

Preferably, several environmental situations are depicted in the image shown, each of these depicted environmental situations being characteristic of different hearing scenarios. The individual hearing scenarios can be selected by the user. The image therefore contains several areas representing typical real-life situations that are representative of different hearing scenarios. These different areas or environmental situations are represented visually, for example by displaying a conversation situation, a playground, a concert hall, a sports arena, a restaurant, etc. These different areas/environmental situations cover different hearing scenarios. For example, more than 3, preferably more than 5 different hearing scenarios are shown in the image.

A hearing scenario is understood to be a complex hearing environment in which several specific hearing situations can typically occur. A specific hearing situation is typically defined by one or more specific sound sources or types of sound sources.

Hearing scenarios include hearing environments such as "office", "concert hall", "children's playground", "sports facility", "restaurant" etc.

Examples of hearing situations are "child's voice(s)", "conversation", "bird's voice", "traffic noise", etc.

Preferably, the section selected by the user, especially the hearing scenario selected by the user, is displayed as a new detail image. In this detail image, different specific hearing situations are offered for selection by the user. If the user selects one of these specific hearing situations, this situation is preferably highlighted again. In particular, the evaluation scale is displayed for this selected specific hearing situation and the hearing value entered by the user is recorded. This version of the system therefore is configured for a multi-stage selection by the user before the evaluation scale is displayed for a specific hearing situation.

This approach is based on the fact that within a typical hearing scenario, e.g. a children's playground, different specific hearing situations, i.e. especially different sound sources, can occur and that these are individually assessed. In this way a more precise setting is achieved. These different specific hearing situations include for example "conversation", "environmental sounds" such as birds or traffic, or "children's voices".

Preferably, a further evaluation scale is displayed, enabling the user to assess the relevance of the selected hearing situation for him with a reference value. This evaluation of the relevance of the respective hearing situation allows conclusions to be drawn about user behaviour.

Alternatively, or in addition to this, the relevance of the different specific hearing situations for the user is automatically derived on the basis of the sections selected by the user, in particular on the basis of the hearing scenarios selected by the user. This is based on the consideration that the user will only select those environmental situations and environmental scenarios from the displayed overall image which are relevant for the user.

The user inputs are evaluated. For this purpose, the following steps in particular are carried out.

Preferably, defined user classes are stored, and the user is assigned to one of the stored user classes on the basis of the inputs of the user, in particular on the basis of the sections selected by the user. The assignment is made in particular on the basis of the hearing scenarios selected by the user. Through the selection, the user reveals something about his general behaviour and also about his lifestyle. This allows the user to be categorised, for example into active or passive person, which also affects the selection of settings.

Preferably, it is determined automatically on the basis of the user's input in which specific hearing situations hearing deficits exist and to what degree. On this basis, the settings for this user, in particular frequency-dependent amplification factors, are then derived.

Furthermore, hearing loss classes are preferably defined and the user is assigned to one of the predefined hearing loss classes based on the hearing values for the specific hearing situations. The hearing loss classes generally classify the type of hearing impairment. This means that each hearing loss class defines a different type of hearing impairment. Possible classes of hearing loss are, for example:
a) Broadband high-frequency loss (hearing deficits in the frequency range from 250 Hz to 1 kHz and additionally in the high-frequency range between 1 kHz and 4 kHz, this applies in particular to speech comprehension),
b) High-frequency steep decay (hearing deficits in the high-frequency range from 1 kHz to 8 kHz with strong decay at higher frequencies), and
c) conductive hearing losses.

The hearing loss classes therefore specifically define hearing deficits in different frequency ranges.

The hearing values for each specific hearing situation generally determine a pair of values, consisting of the selected specific hearing situation, often a specific sound source, and the hearing value of the self-assessment. The respective specific hearing situation can be assigned to one or more hearing loss classes.

In order to assign the user to a hearing loss class, the first method involves adding up the hearing values for the various specific hearing situations to form an overall value and assigning the user to a hearing loss class based on this overall value.

For a more precise classification, the following approach is preferred.

Several hearing loss classes are assigned to a hearing situation, each hearing loss class is weighted with a weighting factor which is specific for the selected hearing situation. Each specific hearing situation is therefore defined by weighted hearing loss classes representing the importance of that particular hearing loss class for that specific hearing situation. The weighting factor is between 0 and 1.

Furthermore, the hearing loss classes assigned and weighted for the different hearing situation are weighted with the hearing value entered by the user for the different hearing situations. Thus, for each hearing situation, a user-specific class value is obtained for the each assigned hearing loss classes. Finally, the individual class values for each hearing loss class are summed up over the various specific hearing situations and an overall class value is obtained for the respective hearing loss class. A total class value is therefore obtained for each hearing loss class. The assignment is then made on the basis of the total class values determined.

For example, the specific hearing situation "conversation" is assigned the hearing loss class "broadband high-frequency loss" with a weighting factor of 1 and the hearing loss class "high-frequency steep decay" with a weighting factor of 0.2. In contrast, the specific hearing situation "children's voices" is assigned the hearing loss classes "broadband high-frequency droop" and "high-frequency steep decay", each with a weighting factor of 0.5.

This assignment can also be understood as a vector, whereby each specific hearing situation is represented by a vector that has several elements. Each element corresponds to a hearing loss class, with each element being assigned a weighting factor. A vector is then multiplied by the hearing value entered for this specific hearing situation. Thereby a class value is obtained for each hearing loss class for the specific hearing situation. The total class value for each hearing loss class is then obtained by adding the vectors. The result is a total class value or a resulting total vector as a measure of the weighted assignment to a hearing loss class. This results in a more differentiated approach, which allows for a more precise adjustment of the hearing aid.

Based on the assignment to one of the hearing loss classes, the setting values are finally derived, especially a frequency-dependent set of gain values. These settings are determined, for example, from a lookup table or an algorithm depending on the assigned hearing loss class.

In addition, critical hearing situations are determined, for which a situation-specific hearing program is selected from a set of pre-defined hearing programs and applied to the hearing aid. In particular, a set of pre-defined parameter difference values is selected. The critical hearing situations are determined on the basis of the assigned user class and/or on the basis of the specific hearing situations in which the user considers his hearing ability to be poor. In this context, poor is understood to mean that the user states his or her hearing ability in the lower half of the evaluation scale offered for self-assessment. This is generally used to identify hearing situations that are critical for the user because of the hearing deficits. A more precise fitting is achieved during operation of the hearing aid by storing such a hearing program that is specifically designed for such a hearing situation. If such a critical hearing situation occurs, the hearing aid is specifically switched to the special hearing program for this specific critical hearing situation. This is typically done by providing difference values which indicate a deviation from the normal setting. The hearing programs are standardized hearing programs and are independent of the specific user. Preferably, the hearing aid contains a so-called classifier, which can automatically distinguish and recognise hearing situations. If such a critical hearing situation is recognised by the classifier, the system automatically switches to the specific hearing program.

Preferably a hearing aid is selected which is suitable for the user based on the user's input. In particular on the basis of the assigned user class and/or the determined hearing loss class. In particular, a suitable hearing aid is selected from various hearing aid types (ITE, BTH, RIC, CIC . . . ). Besides lifestyle information also information about the hearing impairment is taken into account, so that a decision can be made, for example, as to whether the user should be offered an ITE (In The Ear) hearing aid, a RIC/CIC (Receiver/Completely in Canal) hearing aid or a BTH (Behind The Ear) hearing aid.

Finally, the selected hearing aid is configured, i.e. parameterised with the determined setting values. The hearing aid is thereby automatically initially configured.

The hearing aid is then made available to the user. This is done, for example, by delivering it directly to the user.

In summary, the concept presented here makes it easy to configure a hearing aid for the first time, keeping the inhibition threshold as low as possible, especially for first-time users. Such a first-time user can easily determine and configure a suitable hearing aid and have it sent for testing, for example, via a web-based application.

Other features which are considered as characteristic for the invention are set forth in the appended claims.

Although the invention is illustrated and described herein as embodied in a system, a method and a computer program for interactively assisting a user in evaluating a hearing loss, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
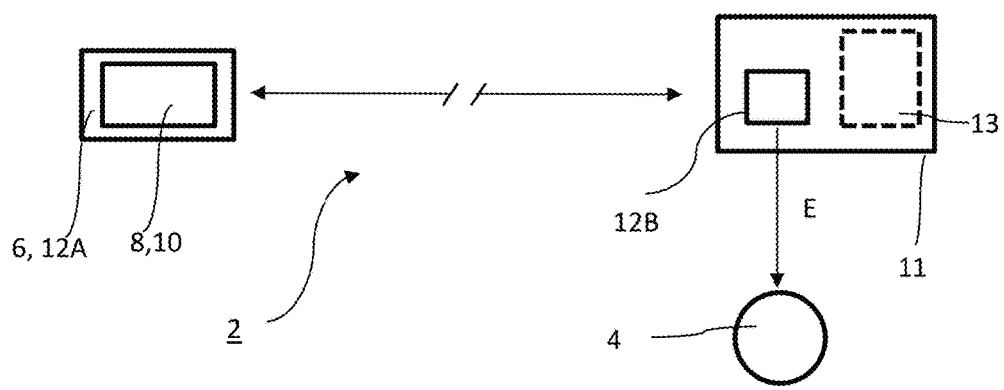
FIG. 1 is a highly simplified illustration of a system for interactively assisting a user during initial configuration of a hearing aid.

Referring now to the figures of the drawings in detail and first, particularly to FIG. 1 thereof, there is shown a system 2 which is used for the interactive support of a user during an initial configuration of a hearing aid 4. In one embodiment according to FIG. 1, the system 2 contains a local user device, such as a tablet 6, which has a display as display element 8, whereby the display element 8 is configured as a touch screen and thus forms an input unit 10. Due to the computing capacity of the tablet 6, it also has a (first) processing unit 12A, which processes the user inputs. In the embodiments indicated in FIG. 1 there is a connection via the Internet to a remote device 11 having a further processing unit 12B. This can be a computer of a manufacturer of hearing aids or a distributor of hearing aids. The two processing units 12A, 12B together form a common processing unit for performing the method and for interactive support of the user. According to a first embodiment there is no assistance by a human.

Alternatively, there is an assistance by a human, especially an audiologist. Especially in this case the remote device has a further display element 13 (shown in dotted lines). The picture shown on the display element 8 is also displayed on the further display element 13, such that the audiologist can follow the user inputs.

Based on the user input, setting values E are determined, which are transferred to hearing aid 4 for configuration. The hearing aid 4 is then delivered to the user. The determination of the setting values can be performed on each of the parts of the processing unit 12A, 12B.

Figure 2A:
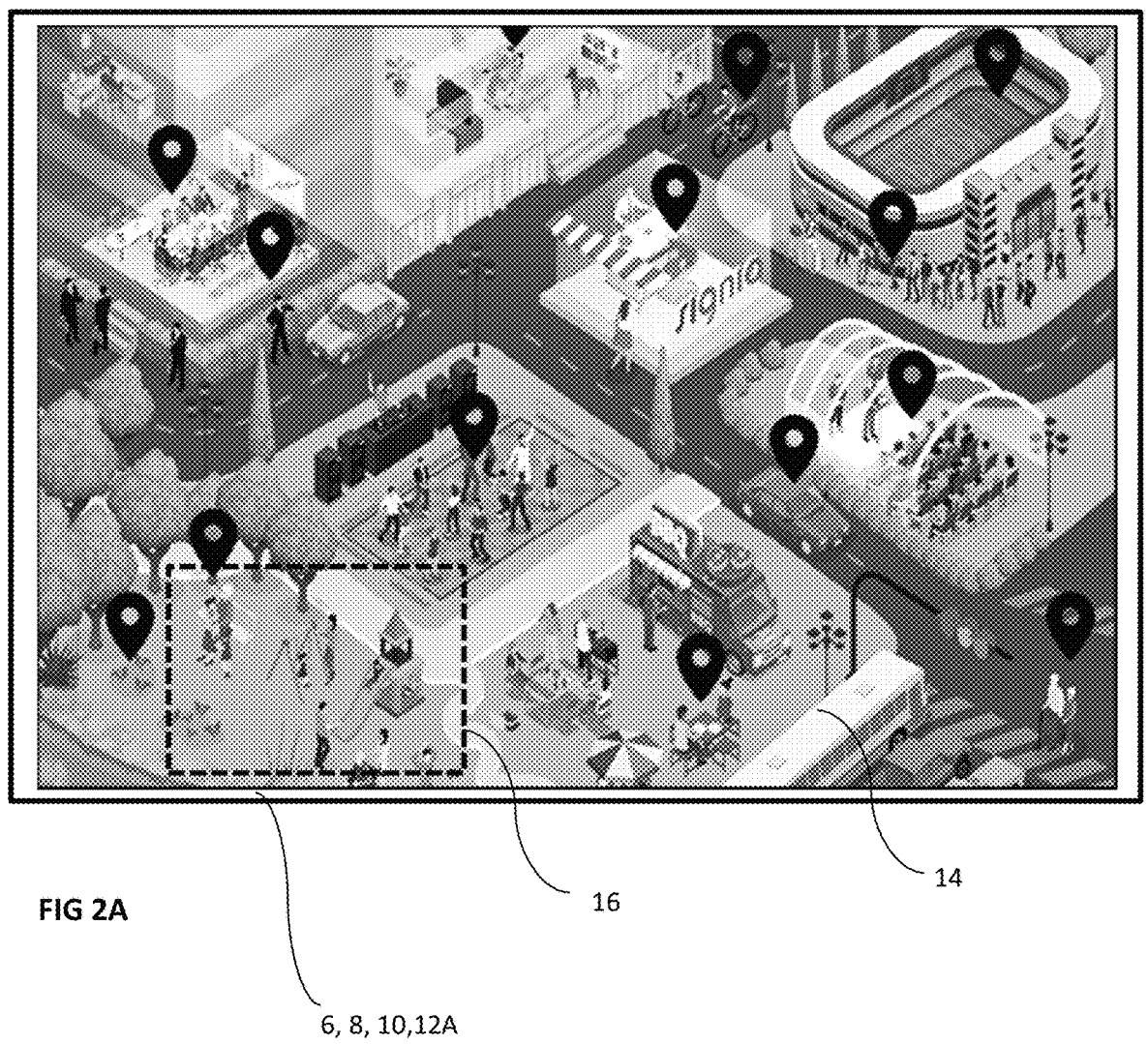
FIG. 2A is a simplified illustration of a display element with an (overall) image with several environmental situations.
Figure 2B:
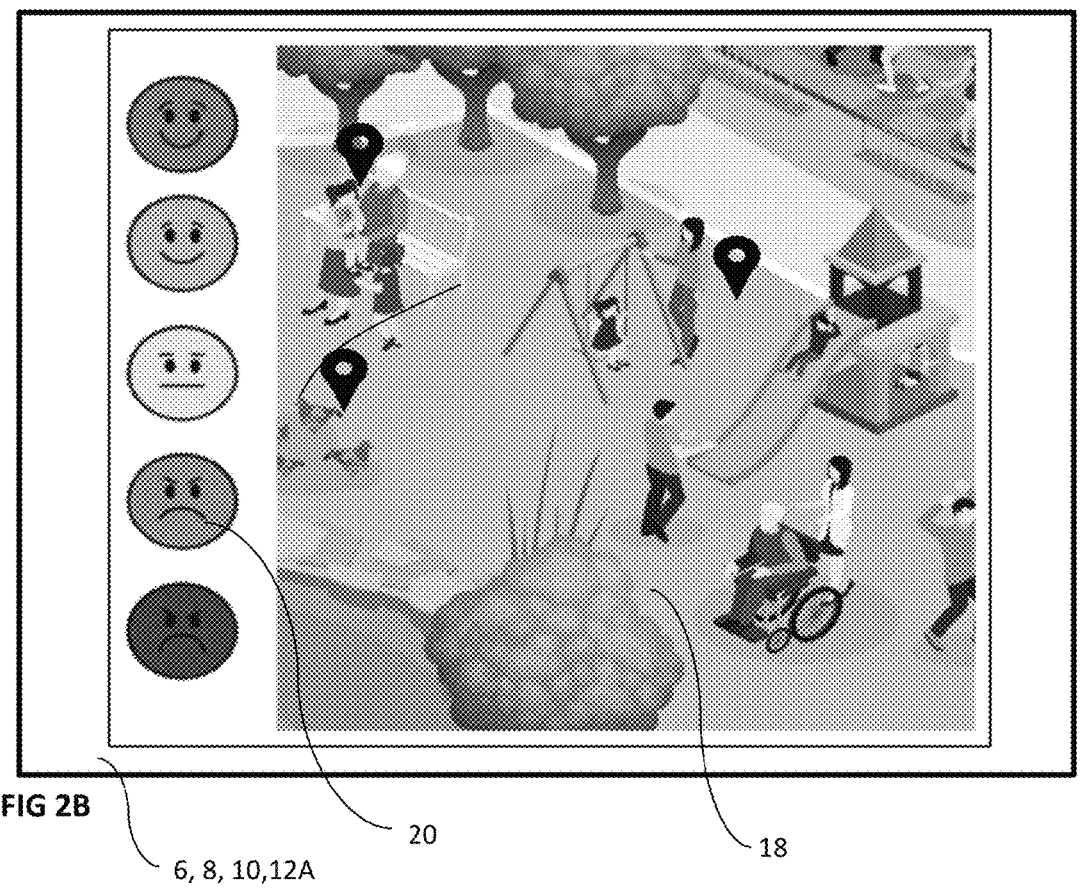
FIG. 2B is an illustration of a display element as shown in FIG. 2A with displaying a detailed image according to a user's selection.
Figure 3A:
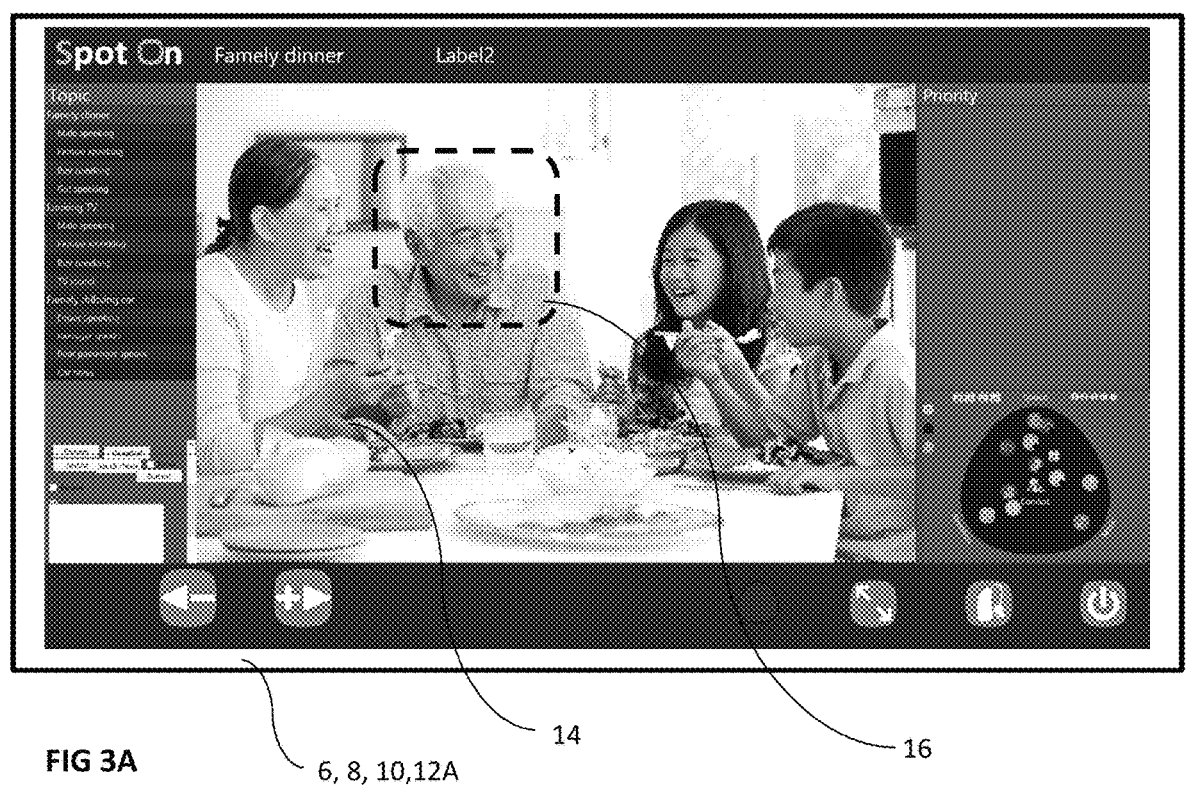
FIG. 3A is an illustration similar to FIG. 2A according to a second variant.
Figure 3B:
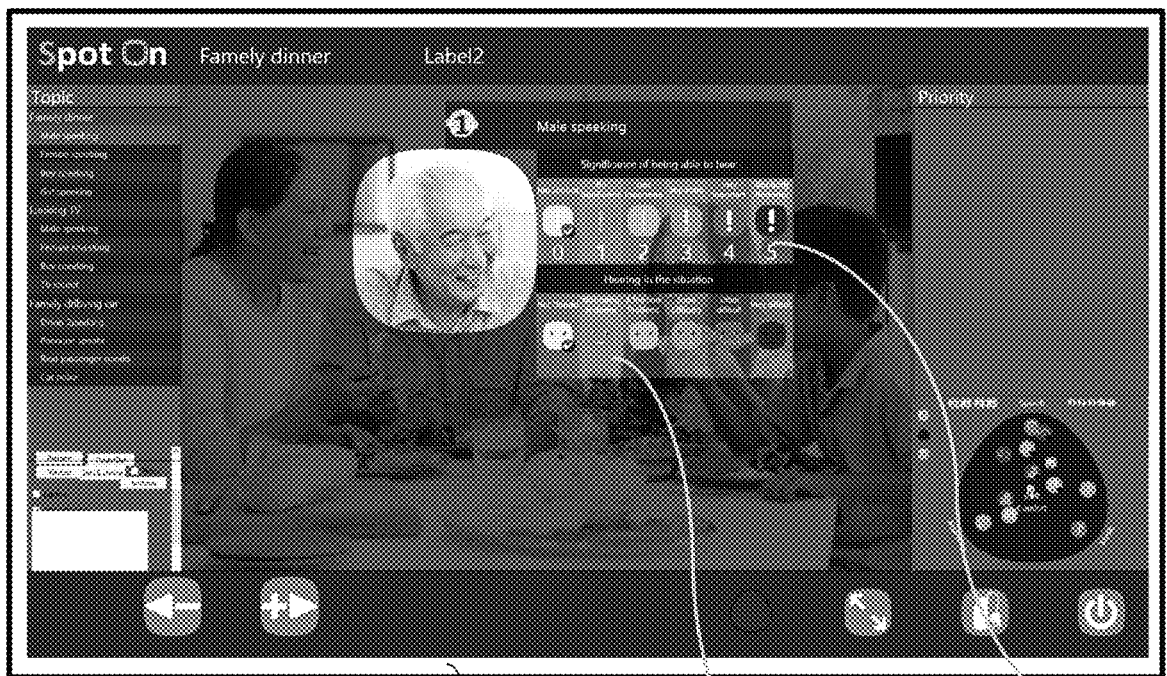
FIG. 3B is an illustration according to FIG. 3A after selection by the user with a highlighted section.

FIGS. 2A, 2B illustrate a first embodiment of a simple graphically assisted support. A second embodiment is illustrated in FIGS. 3A, 3B. Common to both examples is that an image 14 with at least one environmental situation is shown on the display element 8. In both embodiments the user has the possibility to select different environmental situations.

In the first embodiment according to FIG. 2A, image 14 is presented to the user as an overview image, in which different environmental situations are shown, each of which relates to a specific hearing scenario. The overview image is a real image, or at least an animated real image, in which typical everyday situations are shown. These are represented by the natural depiction of different hearing scenarios such as a playground, concert hall, stadium, restaurant, office, road traffic, etc.

The second embodiment shown in FIG. 3A provides a drop-down menu that allows the user to select different environmental situations and thus different hearing scenarios. FIG. 3A shows a situation in which the user has already made a selection. In this case, the user has selected the hearing scenario "family dinner".

In the first embodiment according to FIG. 2A, the user selects a specific hearing scenario by clicking on one of the hearing scenarios shown in overview-image 14. To do this, the user selects a section 16. The selected section 16 is shown in a new detail-image 18, as shown in FIG. 2B. The example shown is the hearing scenario "Children's playground". In this hearing scenario, several specific hearing situations are included, which can be selected by the user. The display element also shows an evaluation scale 20, represented in the example by different smileys. The user uses these smileys to enter a self-assessment of his or her hearing ability for the selected specific hearing situation. Depending on the selection, a hearing value H is recorded for the selected hearing situation. For example, a numerical value is assigned to each image symbol. A higher value, for example, indicates poorer hearing.

The user repeats the selection of a specific hearing situation and the self-assessment preferably for different hearing situations (sound sources) in the selected hearing scenario. Additionally, or alternatively the user repeats the self-Assessment for further hearing scenarios. Therefore, a large number of value pairs are obtained, each value pair representing a specific hearing situation as well as the associated hearing value. Based on these value pairs, the setting values E for the initial setting of hearing aid 4 are derived.

In the second embodiment according to FIGS. 3A, 3B, the first step is to select a hearing scenario. In the representation according to FIG. 3A, the user selects a section 16, which is highlighted in the image. In the second embodiment, this is done in the manner of a spot technique, i.e. the selected section is illuminated in the manner of a cone of light or the rest of the image is darkened. An evaluation scale 20 is displayed in this embodiment too, which the user can use to make a self-assessment and to record the hearing values for the specific hearing situation. In FIG. 3, the specific hearing situation "male voice" was selected as part of the "family dinner" hearing scenario.

In the second embodiment, a further rating scale 22 is displayed, which the user can use to enter an additional relevance value R. According to the user's assessment, the relevance value R indicates the significance of this specific hearing situation, i.e. how important it is for the user to understand the male voice, for example.

In the first embodiment, such a relevance value R is also at least implicitly recorded, namely by the selection of the different hearing scenarios made by the user in overview image 14. On the basis of the selected hearing scenarios and also the non-selected hearing scenarios, a relevance value R can be derived implicitly.

The following procedure is used to evaluate the user's input:

User Class N

In a first step, the user is assigned to a user class N from predefined user classes. The assignment is based on the hearing scenarios selected by the user and/or on the relevance values R entered by the user for the individual hearing situations. A particular specific hearing situation generally corresponds to a typical sound source, such as adult conversation, children's voices, traffic noise, music, birdsong, etc. From this information, conclusions can be drawn about the user's habits, so that the user can be assigned to a user class. A simple differentiation can be made, for example, into the classes "active person" and "passive person".

Hearing Loss Class L

The user is also assigned to a hearing loss class L. The assignment is based on the pairs of values obtained from the user input (hearing situation with assigned hearing value).

Following a simple assignment procedure, the individual hearing values entered by the user are added up and an overall value is obtained. This is a measure of the person's hearing impairment.

A weighting is applied according to a more precise procedure for assignment to a hearing loss class L: A vector is assigned to each specific hearing situation (sound source). The vector consists of individual elements which are weighting factors, each of which is assigned to a hearing loss class. For example, such a vector consists of 2 elements $$v=(L1,L2)$$

where
L1 is the weighted value for hearing loss class 1, for example a broadband high-frequency loss, and
L2 is the weighted value of hearing loss class 2, for example a high-frequency steep decay.

Different hearing situations (sound sources) can be assigned the following vectors, for example:

V1=(1.0, 0.2) for a hearing situation 1, for example "conversation",

V2=(0.5, 0.5) for a hearing situation 2, e.g. "children's voices" and

V3=(0.2, 1.0) for a hearing situation 3 "birds voice".

For example, a first-time user who is affected by a moderate broadband high-frequency decay, so that he or she has hearing deficit in the range of 250 Hz to 1 kHz and also hearing deficits in the range of 1 kHz to 4 kHz, typically has difficulty following conversations because the human voice is located in the range of 1-4 kHz. Children's voices contain more high-frequency components and a bird voice is even higher. This first user will therefore experience the most restrictions in conversations with humans. Accordingly, he or she will, for example, assign a hearing value H1=4 for hearing situation 1 (conversation), a hearing value H2=3 for hearing situation 2 (children's voices) and a hearing value H3=2 for hearing situation 3 ("bird voice"). The individual vectors are weighted and especially multiplied by these hearing values H1, H2, H3. The following vector addition thus results in a total vector, whose individual elements are each formed by a total class value for the respective hearing loss class:

$$4*V1+3*V2+2*V3=(5.9;4.2).$$

It can be seen that the assigned listening values are the typical result of the assessment of a user who has a broadband high-frequency loss. In this respect, the user is assigned to the hearing loss class "broadband high-frequency loss".

In contrast, a second user, for example, is affected by a "high-frequency steep decay", so that he has hardly any hearing deficits in the range of 250 Hz to 1 kHz, but severe hearing deficits in the range of 1 kHz to 8 kHz. He has fewer problems communicating with adults than the previous user. In contrast, he is less able to hear children's voices, and his hearing loss is particularly noticeable when hearing bird voices. Accordingly, he will choose the following hearing values, for example, H1=0, H2=4, H3=5, which results in a total vector in the vector addition as follows:

$$0*V1+4*V2+5*V3=(3.0;7.0).$$

There is therefore an overall class value of 3.0 for the broadband high-frequency hearing loss class and an overall class value of 7.0 for the high-frequency steep-decay hearing loss class. The result is the typical result of the assessment of a person who has a high-frequency steep decay.

This weighted addition of the hearing classes allows a more differentiated assessment to the hearing loss class. Both users have a total value (sum of the individual hearing values) of 9, but different hearing impairments.

Setting Values E

Finally, the setting values E are determined on the basis of hearing loss class L and/or user class N. In particular, a frequency-dependent set of gain settings and, if necessary, compression settings are determined. This is done, for example, by means of a look-up table or in another way, for example, by means of an algorithm, so the method is independent of the audio system which is used by the user.

An important feature of the method is also that (only) predefined standard setting values E are used, which are only designed for different user classes N and/or different hearing loss classes L. In addition, the selection of the setting values is based solely on the user input made by the user. There is no measurement of the hearing deficit e.g. by offering and evaluating sound samples.

Hearing Programs

In addition to the setting values E obtained in this way, one or more specific hearing programs are preferably selected, especially for hearing scenarios or hearing situations that the user has assessed as critical. For example, if the user has given a negative assessment of hearing situations for a specific hearing scenario, such as "office" or "concert hall", a specific hearing program for this hearing scenario is selected from a predefined set of hearing programs and stored. A hearing scenario or a hearing situation is considered negative if the user has made a negative self-assessment of the hearing situation, e.g. if the hearing value exceeds a threshold value. In the case of a hearing scenario, a negative assessment is given, for example, if one or more hearing values entered by the user or their totality for this hearing scenario exceed a specified total value. A particular hearing program is typically defined by a set of differential values. These provide difference values to the standard settings E. When such a hearing program is activated, the standard settings are adjusted by the difference values. The hearing programs are also predefined standard hearing programs that are not individually adapted to the user.

Hearing aid 4 is typically equipped with a so-called classifier, which can identify different hearing scenarios or hearing situations and then select the corresponding assigned hearing program.

Hearing Aid

In a subsequent step, a suitable hearing aid or several suitable hearing aids are determined on the basis of the user input. Preferably both, the determined user class N and the hearing loss class L, are taken into account. In the simplest case, the hearing aid is selected using a lookup table. In particular, the following factors of hearing aids 4 are taken into account: Design, size (form factor), amplification, complexity and ease of use. Thus, hearing loss class L limits the selection of possible hearing aid types. If one has a severe hearing loss, a powerful hearing aid is required. User class N also provides information about the lifestyle of the user.

Different types of hearing aids 4 are typically tailored to different customer groups and thus user classes N and have special features for these special customer groups. Based on the assignment of user class N, the following features, for example, are therefore considered in addition to a basic set up:
a) Adaptive directional microphones,
b) Noise suppression (microphone noise suppression, wind noise suppression . . . ),
c) Sound Smoothing, i.e. a type of acoustic edge smoothing that eliminates short interference peaks (e.g. spoon hits coffee cup),
d) Frequency compression, which transports high-frequency speech components into a lower frequency range (this enables people with a very severe hearing loss in the high frequency range to hear these components in a lower frequency range).

Features outside the signal processing includes, in particular, the following factors:
a) type of hearing aid (ITE, ITE, RIC, CIC . . . ),
b) shape and design of the housing,
c) housing characteristics such as colour, dirt-repellent coating, splash-proof, waterproof, and
d) communication possibilities, such as operation with a remote control, use of a smartphone as a remote control of the hearing aid; Communication with an audio streaming device such as a smartphone to make phone calls, play music, etc. and use the hearing aid as a headset/headphones.

Configuration and Delivery

The previously determined setting values E and, if applicable, the selected hearing programs are then transferred to the selected hearing aid 4 (or several hearing aids 4). This means that the selected hearing aid 4 is configured with an initial setting that allows the user to use the hearing aid 4.

The hearing aid selected and pre-configured is delivered to the user. In principle, several different hearing aids can be supplied for selection.

The following is a summary list of reference numerals and the corresponding structure used in the above description of the invention:
2 System
4 Hearing Aid
6 Tablet
8 Display element
10 Input unit
11 remote device
12A, 12B Processing unit
13 further display element
14 Image
16 Section
18 detailed image
20 evaluation scale
22 further evaluation scale
E Setting value
H Hearing value
R Relevance value
N User class
L Hearing loss class

The invention claimed is:

1. A system for interactively assisting a user in evaluating hearing loss, the system comprising:
a display for presenting an image with at least one environmental situation;
an input unit for detecting user inputs and specifically for selecting a section from the at least one environmental situation;
a processor for controlling said display and for processing the user inputs, said processor being configured such that:
a) the at least one environmental situation is displayed on said display as an image representing a real environment reproduced in a natural manner;
b) based on a user input a selected section of the at least one environmental situation is determined and highlighted;
c) a specific hearing situation is presented pictorially on a basis of a selection made by the user;
d) an evaluation scale is displayed, allowing the user to enter a hearing value for a self-assessment of his\her hearing ability for the specific hearing situation, and the hearing value entered by the user is recorded;
e) steps a) to d) are repeated and hearing values are recorded for different specific hearing situations; and
f) based on the hearing values entered by the user, at least one setting value for a hearing aid is determined.

2. The system according to claim 1, where no sound sample is offered for a determination of the at least one setting value and the at least one setting value is determined based only on the self-assessment made by the user with regard to the different pictorially represented specific hearing situations.

3. The system according to claim 1, further comprising a local device containing said display, said input unit and at least part of said processor.

4. The system according to claim 3, wherein said local device is a tablet or a smartphone.

5. The system according to claim 1, further comprising a remote device having a further display, wherein said processor is configured in such a way that on said display and on said further display the same is displayed.

6. The system according to claim 1, wherein said processor is configured in such a way that the selected section which is selected by the user is highlighted in the image.

7. The system according to claim 1, wherein said processor is configured in such a way that, in the image, several different environmental situations are represented, the several different environmental situations are characteristic of different hearing scenarios and which can be selected by the user and that the selected section is displayed as a new detail image.

8. The system according to claim 1, wherein said processor is configured in such a way that:
for a selected specific hearing situation, a further evaluation scale is displayed allowing the user to enter a relevance value, indicating a relevance of the selected specific hearing situation for the user and the relevance value entered by the user is recorded; and/or
on a basis of the at least one section selected by the user, conclusions are drawn about the relevance of the different specific hearing situations for the user.

9. The system according to claim 1, wherein said processor is configured in such a way that defined user classes are provided and that the user is assigned to one of the defined user classes on a basis of the selection made by the user.

10. The system according to claim 9, wherein said processor is configured in such a way that on a basis of the assigned user class and/or on a basis of the specific hearing situations which the user evaluates as critical, critical hearing situations are determined, for which a specific hearing program is selected from a set of defined hearing programs and stored on the hearing aid.

11. The system according to claim 9, wherein said processor is configured to select the hearing aid suitable for the user on a basis of the user inputs and that an initial setting is automatically made for the hearing aid on a basis of the inputs made by the user.

12. The system according to claim 11, wherein said processor is configured to select the hearing aid suitable for the user on a basis of an user class of the defined user classes assigned to the user.

13. The system according to claim 1, wherein said processor is configured in such a way that hearing loss classes are defined and that the user is assigned to one of the hearing loss classes on a basis of the hearing values.

14. The system according to claim 13, wherein said processor is configured in such a way that, for assignment to a hearing loss class:
the hearing values for the different specific hearing situations are added to form a total value and the assignment to one of the hearing loss classes is effected on a basis of the total value; or
each specific hearing situation is assigned to several of the hearing loss classes, each said hearing loss class is weighted with a weighting factor, for each hearing situation, the hearing loss classes are weighted with the hearing value entered by the user for the hearing situation and thus for each said specific hearing situation a user-specific class value is obtained for each said hearing loss class and the assignment to one of the hearing loss classes is effected on a basis of a user-specific class value.

15. The system according to claim 1, wherein said processor is configured in such a way that setting values are derived on a basis of an assignment to a hearing loss class.

16. The system according to claim 1, wherein the different specific hearing situations are offered therein for selection by the user.

17. A method for interactively assisting a user in evaluating hearing loss, which comprises the steps of:
providing a display for presenting an image with at least one environmental situation;
providing an input unit for detecting user inputs and specifically for selecting a section from a presented environmental situation;
providing a processor for controlling the display and for processing the user inputs, wherein:
a) environmental situations are presented on the display as an image representing a real environment reproduced in a natural manner;
b) based on a user input a selected section of the at least one environmental situation is determined and highlighted;
c) a specific hearing situation is presented pictorially on a basis of a selection made by the user;
d) an evaluation scale is displayed, allowing the user to enter a hearing value for a self-assessment of his\her hearing ability for a specific hearing situation, and the hearing value entered by the user is recorded;
e) steps a) to d) are repeated and hearing values are recorded for different specific hearing situations; and
f) based on the hearing values entered by the user, setting values for a hearing aid are determined.

18. A non-transitory computer readable medium containing computer executable instructions for interactively assisting a user in in evaluating hearing loss and the computer executable instructions which, when executed by a system containing a display for presenting an image with at least one environmental situation, an input unit for detecting user inputs and specifically for selecting a section from the at least one environmental situation, and a processor for controlling the display and for processing the user inputs, cause the system, in response to a user input to execute the following steps:
a) present the environmental situations on the display as an image representing a real environment reproduced in a natural manner;
b) determined and highlight a selected section of the at least one environmental situation based on a user input;
c) present a specific hearing situation pictorially on a basis of a selection made by the user;
d) display an evaluation scale, allowing the user to enter a hearing value for a self-assessment of his\her hearing ability for a specific hearing situation, and the hearing value entered by the user is recorded;
e) repeat steps a) to d) and hearing values are recorded for different specific hearing situations; and
f) determine setting values for a hearing aid based on the hearing values entered by the user.

* * * * *